United States Patent
Hogan

(10) Patent No.: US 7,353,055 B2
(45) Date of Patent: Apr. 1, 2008

(54) NON-INVASIVE ANALYSIS SYSTEM

(76) Inventor: Josh N. Hogan, 620 Kingswood Way, Los Altos, CA (US) 94022

( * ) Notice: Subject to any disclaimer, the term of this patent is extended or adjusted under 35 U.S.C. 154(b) by 0 days.

(21) Appl. No.: 10/870,121

(22) Filed: Jun. 17, 2004

(65) Prior Publication Data

US 2004/0260158 A1    Dec. 23, 2004

Related U.S. Application Data

(60) Provisional application No. 60/479,629, filed on Jun. 18, 2003.

(51) Int. Cl.
A61B 5/00        (2006.01)
A61B 5/1455    (2006.01)

(52) U.S. Cl. ........................................ 600/316; 600/310

(58) Field of Classification Search ................ 600/310, 600/316, 473, 476, 322; 356/450, 451, 456, 356/477, 479
See application file for complete search history.

(56) References Cited

U.S. PATENT DOCUMENTS 6,725,073 B1 * 4/2004 Motamedi et al. .......... 600/316
6,728,571 B1 * 4/2004 Barbato ...................... 600/478

* cited by examiner

*Primary Examiner*—Eric F Winakur

(57) ABSTRACT

A non-invasive analysis system suitable for measuring blood glucose concentration includes a broadband set of coherent beams, with relatively low divergence angle, optical source. It further includes an optical processing system which provides a probe and a reference beam, applies the probe beam to the target to be analyzed, recombines the beams interferometrically and varies the relative phase relationships of the two beams. It further includes control and processing systems.

65 Claims, 5 Drawing Sheets

NON-INVASIVE ANALYSIS SYSTEM

CROSS REFERENCES TO RELATED APPLICATIONS

This application claims priority from provisional application Ser. No. 60/479629 filed on Jun. 18, 2003.

FIELD OF USE

The invention relates to non-invasive optical analysis and in particular to quantitative analysis of analytes, such as glucose.

BACKGROUND

Non-invasive analysis is a valuable technique for acquiring information about systems or targets without undesirable side effects, such as damaging the system being analyzed. In the case of analyzing living entities, such as human tissue, undesirable side effects of invasive analysis include the risk of infection along with pain and discomfort associated with the invasive process. In the particular case of measurement of blood glucose levels in diabetic patients, it is highly desirable to measure the blood glucose level frequently and accurately to provide appropriate treatment of the diabetic condition as absence of appropriate treatment can lead to potentially fatal health issues, including kidney failure, heart disease or stroke. A non-invasive method would avoid the pain and risk of infection and provide an opportunity for frequent or continuous measurement.

Non-invasive analysis based on several techniques have been proposed. These techniques include: near infrared spectroscopy using both transmission and reflectance; spatially resolved diffuse reflectance; frequency domain reflectance; fluorescence spectroscopy; polarimetry and Raman spectroscopy. These techniques are vulnerable to inaccuracies due to issues such as, environmental changes, presence of varying amounts of interfering contamination, skin heterogeneity and variation of location of analysis. These techniques also require considerable processing to de-convolute the required measurement, typically using multivariate analysis and have typically produced insufficient accuracy and reliability.

More recently optical coherence tomography (OCT), using a super-luminescence diode (SLD) as the optical source, has been proposed in Proceedings of SPIE, Vol. 4263, pages 83-90 (2001). The SLD output beam has a broad bandwidth and short coherence length. The technique involves splitting the output beam into a probe and reference beam. The probe beam is applied to the system to be analyzed (the target). Light scattered back from the target is combined with the reference beam to form the measurement signal.

Because of the short coherence length only light that is scattered from a depth within the target such that the total optical path lengths of the probe and reference are equal combine interferometrically. Thus the interferometric signal provides a measurement of the scattering value at a particular depth within the target. By varying the length of the reference path length, a measurement of the scattering values at various depths can be measured and thus the scattering value as a function of depth can be measured.

The correlation between blood glucose concentration and scattering has been reported in Optics Letters, Vol. 19, No. 24, Dec. 15, 1994 pages 2062-2064. The change of the scattering value as a function of depth correlates with the glucose concentration and therefore measuring the change of the scattering value with depth provides a measurement of the glucose concentration. Determining the glucose concentration from a change, rather than an absolute value provides insensitivity to environmental conditions.

However, SLDs emit incoherent light that consists of amplified spontaneous emissions with associated wide angle beam divergence which have the undesirable beam handling and noise problems. The beam is also a continuous wave (CW) source with no opportunity for temporal based signal enhancement. Also, because of the random nature of spontaneous emission, the reference signal must be derived from same SLD signal and have equal optical path length as the probe signal. Therefore, without an opportunity to avail of multiple sources, the relative optical path length must be physically changed by a scanning mechanism and the reference path length must be of similar magnitude to the probe path length. Typical electro-mechanical scanning techniques have limited scan speeds which makes conventional OCT systems critically vulnerable to relative motion between the analyzing system and the target. These aspects cause systems based on SLD sources to have significantly lower signal to noise characteristics and present problems in practical implementations with sufficient accuracy, compactness and robustness for commercially viable and clinically accurate devices.

Therefore there is an unmet need for commercially viable, compact, robust, non-invasive device with sufficient accuracy, precision and repeatability to measure analyte characteristics, and, in particular, to measure glucose concentration in human tissue.

SUMMARY OF THE INVENTION

The invention is a method, apparatus and system for non-invasive analysis suitable for measuring blood glucose concentration. The invention includes an optical source comprised of a broadband set of coherent beams, with relatively low divergence angle. It further includes an optical processing system which provides a probe and a reference beam; the system applies the probe beam to the target to be analyzed, recombines the beams interferometrically and varies the relative temporal relationship of the coherence phase of the two beams. It further includes control and processing systems.

DETAILED DESCRIPTION OF THE INVENTION

Figure 1:
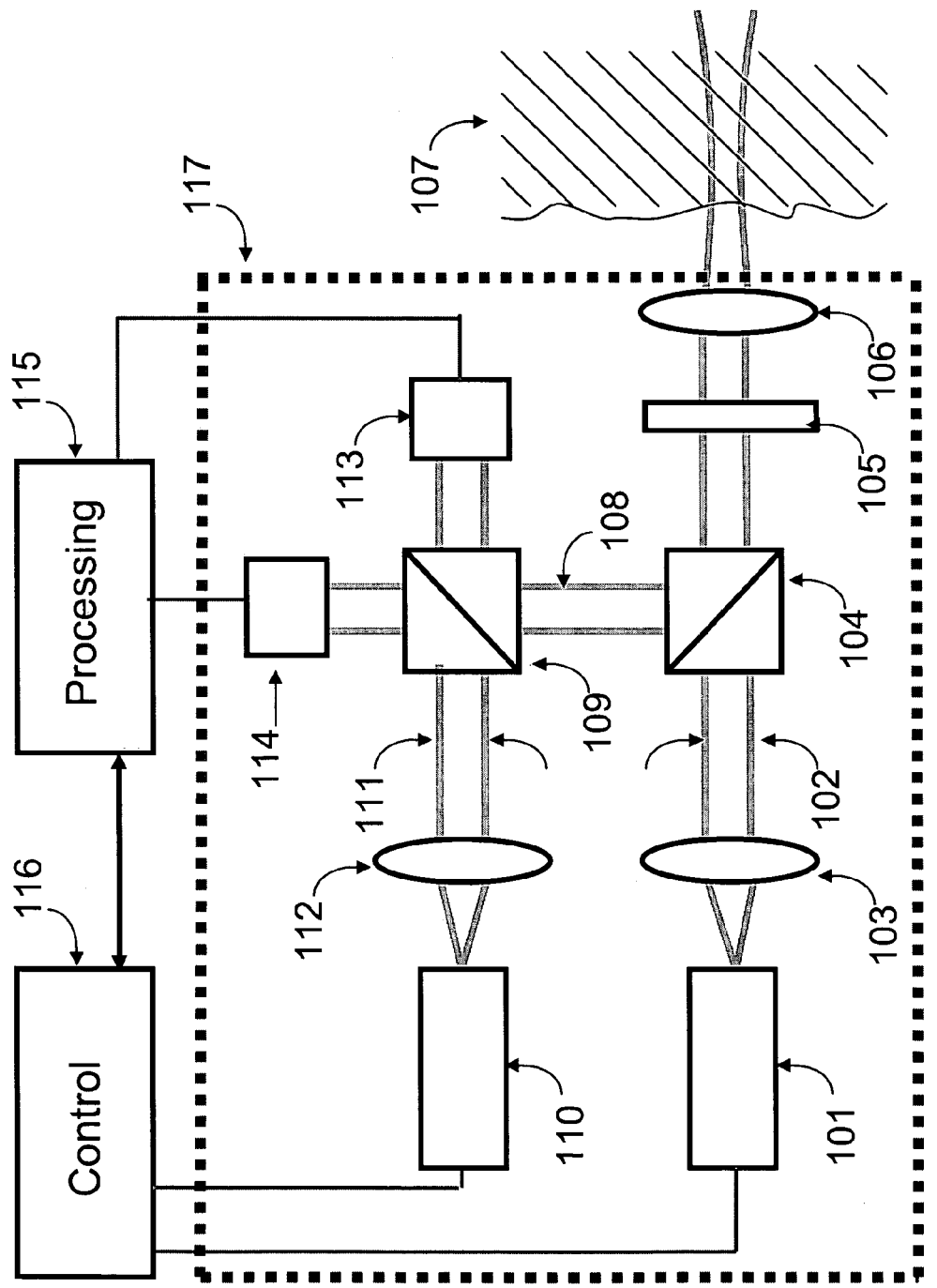
FIG. 1 is an illustration of the non-invasive analysis system according to the invention.

Conventional optical coherence tomography is based on a source having a broad band of incoherent wavelengths, with the problems and limitations described above. An alternative approach, which addresses these problems and limitations, is to use a source having a broad set of discrete coherent wavelengths. A preferred embodiment of this invention is illustrated in and described with reference to FIG. 1 where a non-invasive optical analysis system is shown.

The system described in this preferred embodiment is designed to analyze the characteristics of analytes, in particular, the concentration of glucose in human tissue. The system includes a first electronically pumped and mode-locked laser diode 1011, whose output 102, herein referred to as a repetitive discrete coherent optical signal or "probe signal", consists of a broad band set of wavelengths or modes that have a repetitive phase relationship with each other. The repetitive discrete coherent optical signal or "probe signal" is collimated by a first lens 103.

The repetitive discrete coherent optical signal or "probe signal" 102 is passed through a first beam splitter 104, such as a polarization beam splitter, through a quarter wave plate 105, and a second lens 106, with a relatively long Rayleigh range, e.g. 1 mm, and focused in a target 107. At least part of the repetitive discrete coherent optical signal or "probe signal" 102 applied to the target is scattered back and captured by the second lens 106. Scattering occurs because of discontinuities, such as changes of refractive index. A scattered portion of the repetitive discrete coherent optical signal or "probe signal" 102 passes through the quarter waveplate 105, back to the first beam-splitter 104 and at least a part of the captured scattered signal 108 is directed to a second beam splitter 109.

A second electronically mode-locked laser diode 110 outputs a reference optical signal 111 which is collimated by a third lens 112 and is also directed to the second beam splitter 109, where it is combined interferometrically with the captured scattered signal 108.

The resulting interference signal is detected by first and second opto-electronic detectors 113 and 114 and processed by an processing module 115. A single opto-electronic detector may be used. An advantage of using a first and a second opto-electronic detector is that it provides a means to suppress noise by exploiting the complementary nature of the signals and having them detected differentially. A control module 116 controls the mode-locked operation of the first and second laser diodes 101 and 110 and also provides timing information to the processing module 115. The processing module 115 combines this timing information with the detected interference signals to compute scattering profiles as a function of depth within the target.

The control module 116, along with the processing module 115, combines the computed scattering profiles as a function of depth with previously stored information relating such profiles to glucose concentration, to determine the current glucose concentration. The control module 116 also stores the processed, computed and determined information and control parameters in non-volatile memory for display, for further analysis and future operation.

The optical components, 101, 103, 104, 105, 106, 109, 110, 112, 113 and 114, enclosed by the dashed box 117 in FIG. 1, do not involve any moving parts. The system can be assembled, for example, on an optical micro-bench so as to produce a portable, compact, and continuously measuring device.

Figure 2:
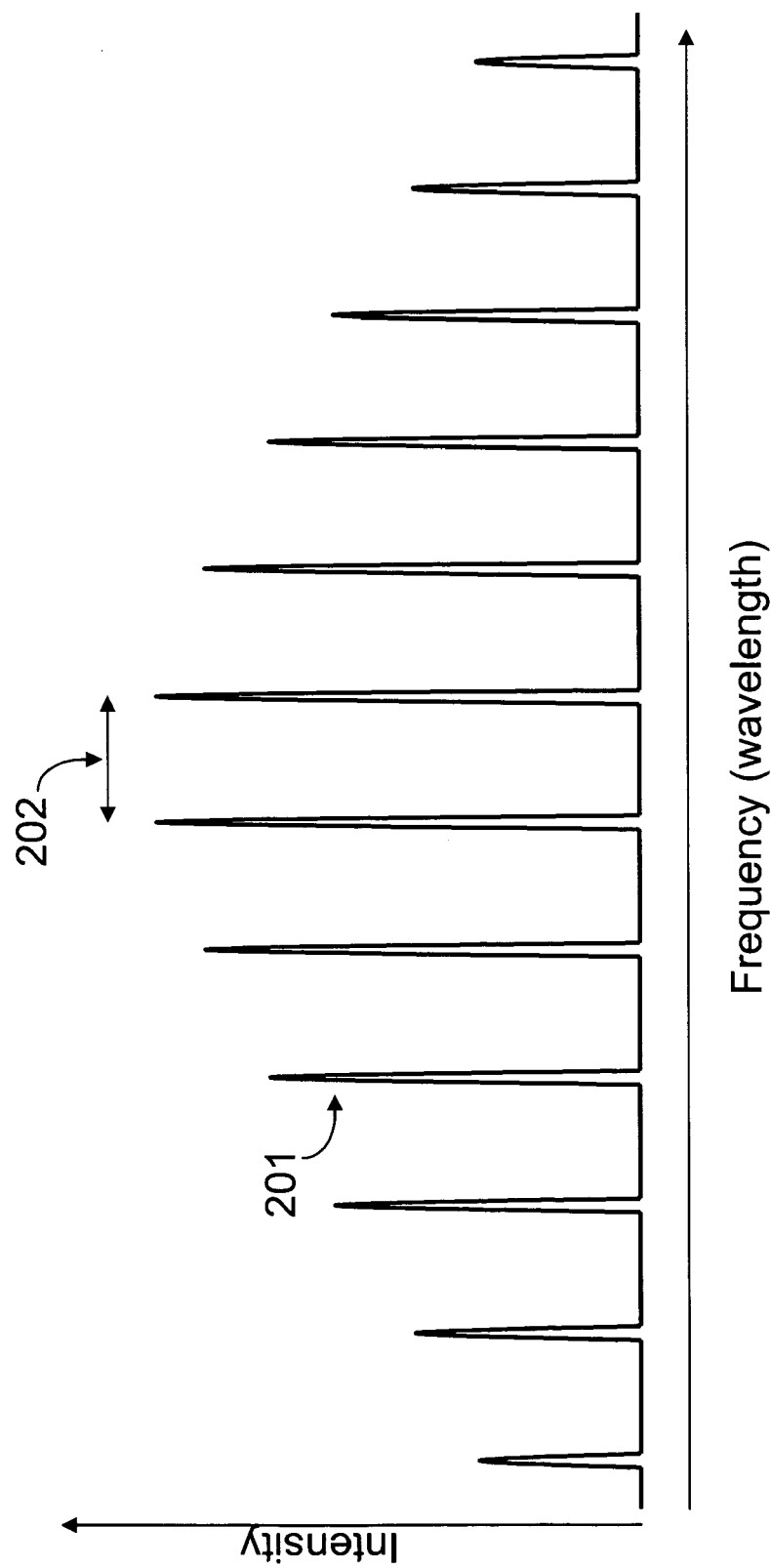
FIG. 2 is a frequency domain illustration of an output of a mode-locked laser optical source.

The output of a mode-locked laser diode is further illustrated in the frequency domain in FIG. 2 and consists of a set of modes, one of which is 201, which are separated from each other by a constant frequency difference 202. This frequency difference (delta_F) is related to the length of the laser diode according to the relationship $delta\_F = c/(2 nL)$ where c is the speed of light, n is the refractive index of the lasing material and L is the length of the laser diode cavity.

Figure 3:
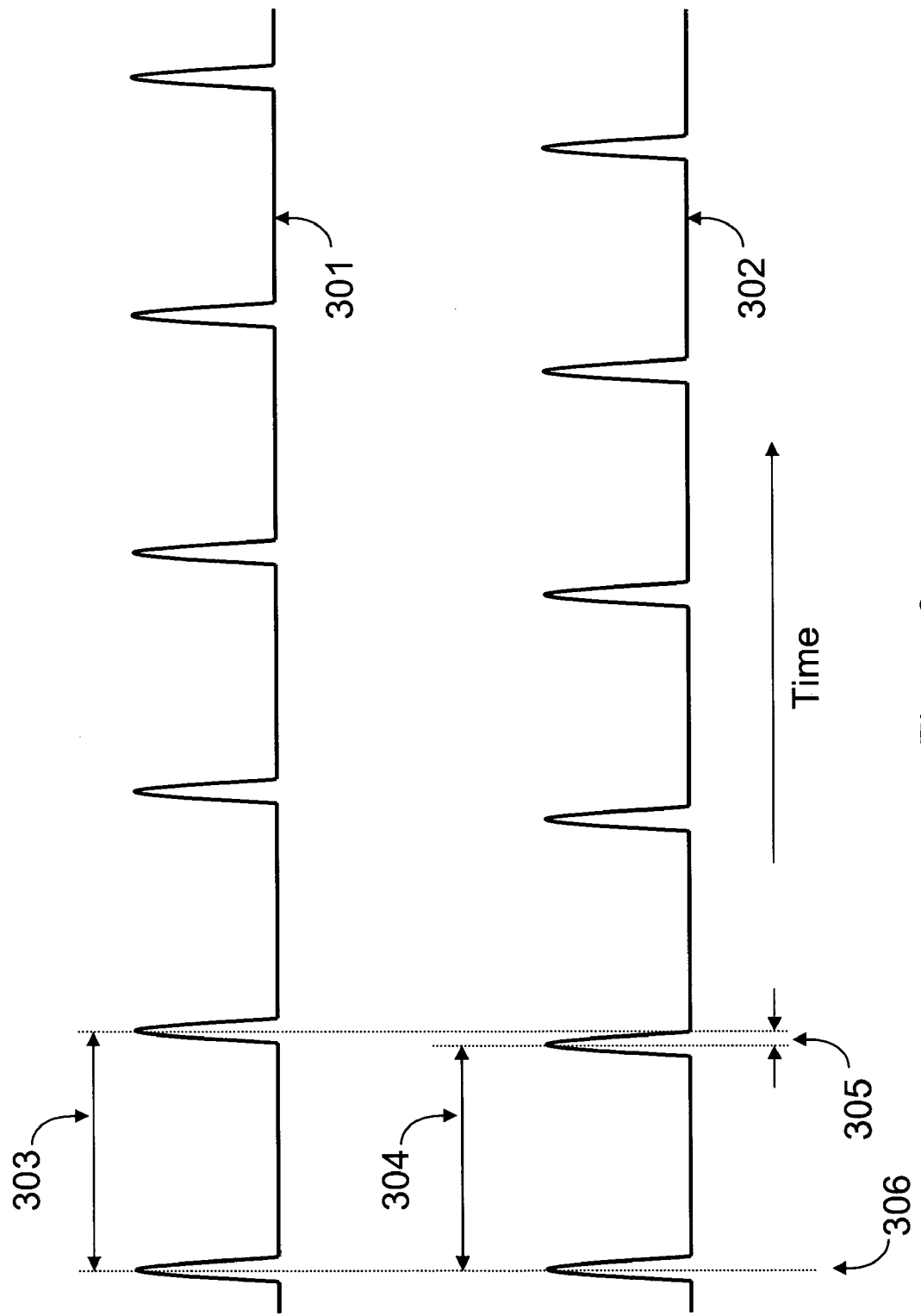
FIG. 3 is a time domain illustration of the outputs of mode-locked laser optical sources.

Mode-locking is achieved by modulating the laser diode at a frequency equal to or harmonically related to the frequency delta_F. The output of the first laser diode 101, of FIG. 1, referred to as the repetitive discrete coherent optical signal or "probe signal" 102 is illustrated in the time domain in FIG. 3, where it is shown as a first pulse train 301 with a first repetition period 303, (T1) which is the reciprocal of its repetition frequency delta_F1 (or pulse frequency). The output of the second laser diode 110, of FIG. 1, is shown as a second pulse train 302 with a second repetition period 304, (T2) which is the reciprocal of its frequency delta_F2.

The difference between the first and second repetition periods 305 corresponds to the difference between the two frequencies delta_F1 and delta_F2, which is referred to as a frequency offset. Pulses from the two pulse trains go from being aligned in time, as shown at point 306, to a systematic increase in misalignment until the pulses come back into alignment. The frequency with which pulses come back into alignment is related to the frequency offset. The varying temporal relative alignment of the two pulse trains is referred to as their "temporal coherence phase relationship".

Referring again to FIG. 1, when the captured scattered optical signal 108 is combined with the reference optical signal 111, an interference signal will only exist when the captured scattered optical signal is substantially aligned in time with the reference optical signal 111. Because the reference optical and captured scattered signals have different pulse frequencies, at any given time, this alignment will correspond to only the optical signal scattered from a particular depth within the target.

Thus, having a frequency offset between the reference and probe signals has the effect of selectively discriminating in favor of detecting a signal scattered from different depths in the target at different times. This effectively provides an electronic method of scanning in depth (or in the z-axis), using a system that has no moving parts. The range of the scan corresponds to the optical path length of the laser cavity. A full scan occurs with a frequency corresponding to the frequency offset.

The optical system 107 in FIG. 1 can then be translated in a direction perpendicular to the z-axis by conventional electromechanical techniques, to provide a two dimensional scan of the target.

The control module 116 in FIG. 1 generates the electronic signals to mode-lock both the first and second laser diodes 101 and 110 and provides a signal representing the frequency off set between them to the processing module 115. This signal represents the temporal coherence phase relationship between the reference and probe signals. This allows the processing module 115 to determine from what depth in the target the detected interferometric signal was scattered.

The frequency offset between the two mode locked lasers can be sufficiently high to permit depth scan rates that are fast compared to typical motion artifacts. It may be low enough that corresponding wavelengths from the sets of wavelengths output by the two mode locked lasers have substantially the same wavelength values.

Figure 4:
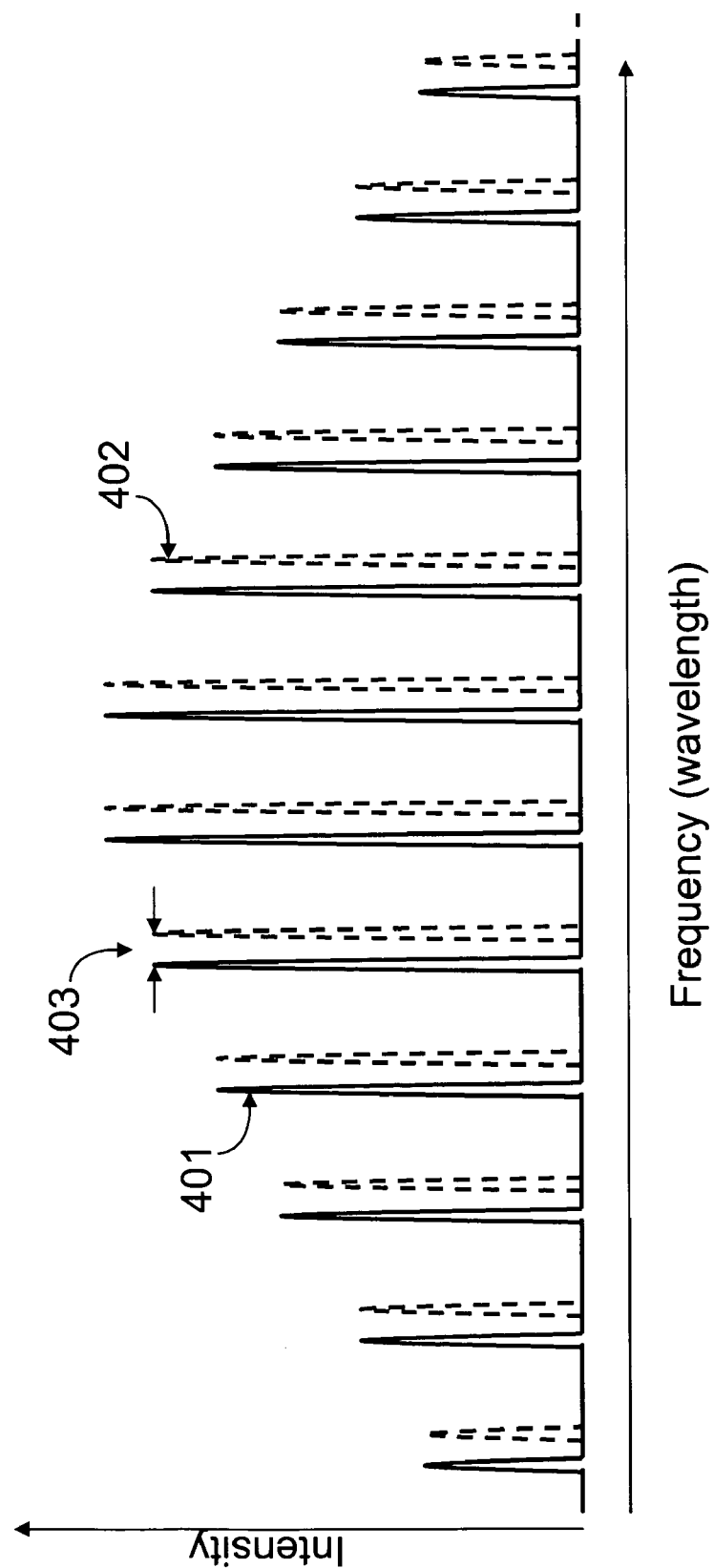
FIG. 4 is a frequency domain illustration of outputs of two mode-locked laser optical sources.

The two wavelength sets can optionally have a frequency offset, that is substantially the same for all corresponding wavelengths from the two sets. In FIG. 4 the outputs of two mode-locked lasers are illustrated in the frequency domain and consist of a first set of modes, one of which is 401, and a second set of modes, one of which is 402. (The second set of modes or wavelengths is illustrated by dashed lines.) These are offset by a frequency offset 403 that is substantially the same for all corresponding modes (or wavelengths)

of the two sets. This offset enables more sophisticated signal detection techniques, including but not limited to coherent heterodyne techniques.

In an alternative embodiment, depth scanning can be accomplished by varying the temporal relationship between the captured scattered signal and the reference optical signal by modifying the coherence phase offset between the first and second mode locked lasers. This can be done by, for example, having both lasers mode locked at substantially the same frequency and varying the phase relation between RF (radio frequency) signals electronically mode locking the lasers.

Figure 5:
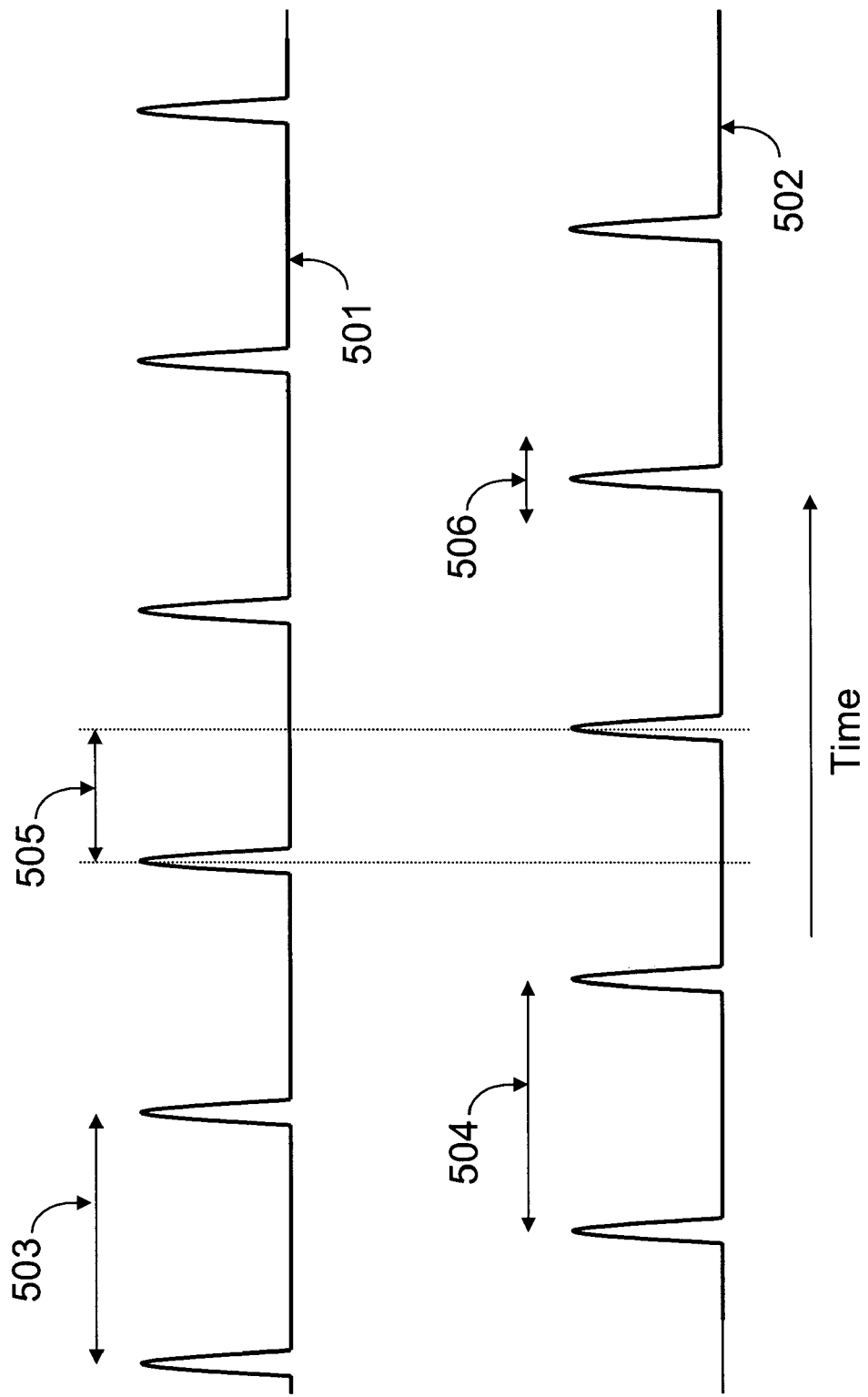
FIG. 5 is an alternate time domain illustration of the outputs of mode-locked laser sources.

Typical outputs of the lasers in such an embodiment are illustrated in FIG. 5, where the first laser output 501 and the second laser output 502 have substantially the same repetition rate indicated by the periods 503 and 504. The temporal phase coherence relationship between the two pulse trains 505 is aligned so the pulse trains are substantially 180 degrees out of phase when the signals are combined interferometrically.

Scanning is accomplished by varying this phase relationship by an amount, for example, indicated by 506. The scanning frequency is determined by the frequency with which the phase coherence is modulated. The scanning range is determined by the magnitude of the phase coherence variation 506.

It is understood that the above description is intended to be illustrative and not restrictive. Many of the features have functional equivalents that are intended to be included in the invention as being taught.

For example, the mode locked laser could be optically pumped, it could be a solid state laser, such as a Cr:LiSAF laser optically pumped by a diode laser and it could be passively mode locked by a Kerr lens or a semiconductor saturable absorber mirror.

Gain switched optical sources, with optical feedback to lock modes may also be used. For purposes of this invention, mode-locked lasers will include gain switched optical sources.

Other examples will be apparent to persons skilled in the art. The scope of this invention should therefore not be determined with reference to the above description, but instead should be determined with reference to the appended claims, along with the full scope of equivalents to which such claims are entitled.

What is claimed is:

1. A method for non-invasive measurement of an analyte in a target comprising:
    generating a first repetitive discrete coherent optical signal wherein the first repetitive discrete coherent optical signal is generated by a first mode-locked laser;
    applying at least part of said optical signal to the target to be analyzed, a portion of which will be scattered by the target;
    capturing at least part of said optical signal scattered by the target;
    generating a second repetitive discrete coherent optical signal wherein the second repetitive discrete coherent optical signal is a reference optical signal generated by a second mode-locked laser;
    combining the captured scattered optical signal with said reference optical signal;
    modifying the temporal coherence phase relationship between the captured scattered optical signal and said reference optical signal;
    detecting an interference signal between the captured scattered optical signal and said reference optical signal;
    analyzing the detected interference signal at multiple temporal relationships; and
    determining the analyte measurement.

2. The method of claim 1, wherein the first mode-locked laser is a mode-locked semiconductor laser.

3. The method of claim 1, wherein the first mode-locked laser is electronically pumped.

4. The method of claim 1, wherein the first mode-locked laser is optically pumped by a semiconductor laser diode.

5. The method of claim 1, wherein the first mode-locked laser is a Cr:LiSAF laser.

6. The method of claim 1, wherein at least a part of the generated optical signal is focused in the target to be analyzed by means of a lens with a long Rayleigh focus range.

7. The method of claim 6, wherein the Rayleigh range is of the order of one or more millimeters.

8. The method of claim 1, wherein part of the generated optical signal is scattered by discontinuities in the target.

9. The method of claim 8, wherein the discontinuities in the target are caused by changes of refractive index.

10. The method of claim 1, wherein the captured scattered signal is captured by the focusing lens.

11. The method of claim 1, wherein the captured scattered signal is separated from the first generated optical signal by means of a polarization separator.

12. The method of claim 1, wherein the second mode locked laser has a mode locking frequency offset from the first mode locked laser.

13. The method of claim 1, wherein the second mode locked laser has substantially the same wavelength range and substantially the same mode locking frequency as the first mode locked laser.

14. The method of claim 1, wherein the second mode locked laser has wavelength values offset from the wavelength values of the first mode locked laser by an offset that is substantially the same for all corresponding wavelengths.

15. The method of claim 1, wherein the coherence phase of the second mode locked laser is phase offset from the coherence phase of the first mode locked laser.

16. The method of claim 1, wherein the temporal relationship between the captured scattered signal and the reference optical signal is modified by modifying the coherence phase offset between the first and second mode locked lasers.

17. The method of claim 1, wherein the temporal relationship between the captured scattered signal and the reference optical signal is modified by means of the frequency offset between the first and second mode locked lasers.

18. The method of claim 1, wherein the temporal relationship between the captured scattered signal and the reference optical signal is modified by modifying the relative optical path difference between the captured scattered and reference optical signals.

19. The method of claim 1, wherein the captured scattered signal and the reference optical signal are combined interferometrically.

20. The method of claim 1, wherein the interference signal between the captured scattered and reference optical signals is detected by means of an opto-electronic detector.

21. The method of claim 1, wherein the interference signal between the captured scattered and reference optical signals is detected differentially by means of two opto-electronic detectors.

22. The method of claim 1, wherein the interference signals are detected by means of at least one opto-electronic detector at multiple temporal relationships between the captured scattered and reference optical signals.

23. The method of claim 1, wherein the detected signals are combined with electronic signals aligned with the coherence phase of the reference optical signal.

24. The method of claim 1, wherein the detected signals are analyzed by means of combining information from detected signals at at least two temporal relationships between the captured scattered and reference optical signals.

25. The method of claim 24, wherein the detected signals are analyzed to determine the detected signals as a function of the temporal relationships between the captured scattered and reference optical signals.

26. The method of claim 25, wherein the detected signals as a function of the temporal relationships between the captured scattered and reference optical signals are analyzed by an electronic processing system to determine an analyte characteristic within the target.

27. The method of claim 1, wherein a control system coordinates the temporal relationships between the captured scattered and reference optical signals, electronic signals aligned with the coherence phase of the reference optical signal, the detected signals and the processing system.

28. The method of claim 1, wherein the control system stores control parameters in electronic memory.

29. The method of claim 1, wherein the control system stores processed information in electronic memory.

30. The method of claim 1, wherein the analyte is glucose.

31. The method of claim 1, wherein the target is human tissue.

32. The method of claim 1, wherein the measurement is made continuously.

33. A system for non-invasive measurement of a characteristic of a target comprising:
   a first mode locked laser operable to generate a first repetitive discrete coherent optical signal;
   a lens operable to apply at least part of said optical signal to the target to be analyzed, a portion of which will be scattered by the target and to capture at least part of said optical signal scattered by the target;
   a second mode locked laser operable to generate a second repetitive discrete coherent optical signal wherein the second repetitive discrete coherent optical signal is a reference optical signal;
   a beam splitter operable to combine the captured scattered optical signal with said reference optical signal;
   an electronic module operable to modify the temporal coherence phase relationship between the captured scattered optical signal and said reference optical signal;
   a detector operable to detect an interference signal between the captured scattered signal and said reference optical signal;
   an electronic processing module operable to analyze the detected interference signal at multiple temporal relationships and operable to determine the measurement of the characteristic.

34. An apparatus for non-invasively measuring of an analyte in a target comprising:
   means for generating a first repetitive discrete coherent optical signal wherein the first repetitive discrete coherent optical signal is generated by a first mode locked laser;
   means for applying at least part of said optical signal to the target to be analyzed, a portion of which will be scattered by the target;
   means for capturing at least part of said optical signal scattered by the target;
   means for generating a second repetitive discrete coherent optical signal wherein the second repetitive discrete coherent optical signal is a reference optical signal generated by a second mode locked laser;
   means for combining the captured scattered optical signal with said reference optical signal;
   means for modifying the temporal coherence phase relationship between the captured scattered optical signal and said reference optical signal;
   means for detecting an interference signal between the captured scattered optical signal and said reference optical signal;
   means for analyzing the detected interference signal at multiple temporal relationships; and
   means for determining the analyte measurement.

35. The apparatus of claim 34, wherein the first mode locked laser is a mode locked semiconductor laser.

36. The apparatus of claim 34, wherein the first mode-locked laser is electronically pumped.

37. The apparatus of claim 34, wherein the first mode-locked laser is optically pumped by a semiconductor laser diode.

38. The apparatus of claim 34, wherein the first mode locked laser is a Cr:LiSAF laser.

39. The apparatus of claim 34, wherein at least a part of the generated optical signal is focused in the target to be analyzed by means of a lens with a long Rayleigh focus range.

40. The apparatus of claim 39, wherein the Rayleigh range is of the order of one or more millimeters.

41. The apparatus of claim 34, wherein part of the generated optical signal is scattered by discontinuities in the target.

42. The apparatus of claim 41, wherein the discontinuities in the target are caused by changes of refractive index.

43. The apparatus of claim 34, wherein the captured scattered signal is captured by the focusing lens.

44. The apparatus of claim 34, wherein the captured scattered signal is separated from the first generated optical signal by means of a polarization separator.

45. The apparatus of claim 34, wherein the second mode locked laser has a mode locking frequency offset from the first mode locked laser.

46. The apparatus of claim 34, wherein the second mode locked laser has substantially the same wavelength range and substantially the same mode locking frequency as the first mode locked laser.

47. The apparatus of claim 34, wherein the second mode locked laser has wavelength values offset from the wavelength values of the first mode locked laser by an offset that is substantially the same for all corresponding wavelengths.

48. The apparatus of claim 34, wherein the coherence phase of the second mode locked laser may be phase offset from the coherence phase of the first mode locked laser.

49. The apparatus of claim 34, wherein the temporal relationship between the captured scattered signal and the reference optical signal is modified by modifying the coherence phase offset between the first and second mode locked lasers.

50. The apparatus of claim 34, wherein the temporal relationship between the captured scattered signal and the reference optical signal is modified by means of the frequency offset between the first and second mode locked lasers.

51. The apparatus of claim 34, wherein the temporal relationship between the captured scattered signal and the reference optical signal is modified by modifying the relative optical path difference between the captured scattered and reference optical signals.

52. The apparatus of claim 34, wherein the captured scattered signal and the reference optical signal are combined interferometrically.

53. The apparatus of claim 34, wherein the interference signal between the captured scattered and reference optical signals is detected by means of an opto-electronic detector.

54. The apparatus of claim 34, wherein the interference signal between the captured scattered and reference optical signals is detected differentially by means of two opto-electronic detectors.

55. The apparatus of claim 34, wherein the interference signals are detected by means of at least one opto-electronic detector at multiple temporal relationships between the captured scattered and reference optical signals.

56. The apparatus of claim 34, wherein the detected signals are combined with electronic signals aligned with the coherence phase of the reference optical signal.

57. The apparatus of claim 34, wherein the detected signals are analyzed by means of combining information from detected signals at least two temporal relationships between the captured scattered and reference optical signals.

58. The apparatus of claim 57, wherein the detected signals are analyzed to determine the detected signals as a function of the temporal relationships between the captured scattered and reference optical signals.

59. The apparatus of claim 58, wherein the detected signals as a function of the temporal relationships between the captured scattered and reference optical signals are analyzed by an electronic processing system to determine an analyte characteristic within the target.

60. The apparatus of claim 34, wherein a control system coordinates the temporal relationships between the captured scattered and reference optical signals, electronic signals aligned with the coherence phase of the reference optical signal, the detected signals and the processing system.

61. The apparatus of claim 34, wherein the control system stores control parameters in electronic memory.

62. The apparatus of claim 34, wherein the control system stores processed information in electronic memory.

63. The apparatus of claim 34, wherein the analyte is glucose.

64. The apparatus of claim 34, wherein the target is human tissue.

65. The apparatus of claim 34, wherein the measurement is made continuously.

* * * * *